US009539333B2

(12) United States Patent
Dunn

(10) Patent No.: US 9,539,333 B2
(45) Date of Patent: *Jan. 10, 2017

(54) SUSTAINED RELEASE POLYMER

(71) Applicant: Tolmar Therapeutics, Inc., Fort Collins, CO (US)

(72) Inventor: Richard L. Dunn, Fort Collins, CO (US)

(73) Assignee: Tolmar Therapeutics, Inc., Fort Collins, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/014,810

(22) Filed: Feb. 3, 2016

(65) Prior Publication Data

US 2016/0220682 A1 Aug. 4, 2016

Related U.S. Application Data

(63) Continuation of application No. 14/463,353, filed on Aug. 19, 2014, now Pat. No. 9,283,282, which is a continuation of application No. 13/900,338, filed on May 22, 2013, now Pat. No. 8,840,916, which is a continuation of application No. 11/469,392, filed on Aug. 31, 2006, now Pat. No. 8,470,359, which is a continuation-in-part of application No. 10/872,671, filed on Jun. 21, 2004, now abandoned, which is a continuation of application No. 10/373,400, filed on Feb. 24, 2003, now Pat. No. 6,773,714, which is a continuation of application No. 09/711,758, filed on Nov. 13, 2000, now Pat. No. 6,565,874.

(51) Int. Cl.
| | |
|---|---|
| A61K 31/519 | (2006.01) |
| A61K 47/34 | (2006.01) |
| C08L 67/04 | (2006.01) |
| A61K 9/51 | (2006.01) |
| A61K 9/16 | (2006.01) |
| C08L 67/02 | (2006.01) |
| A61K 9/00 | (2006.01) |
| C08G 63/00 | (2006.01) |
| A61J 1/20 | (2006.01) |
| A61K 38/08 | (2006.01) |
| A61K 47/22 | (2006.01) |
| A61K 38/09 | (2006.01) |
| C08G 63/08 | (2006.01) |
| A61K 47/48 | (2006.01) |

(52) U.S. Cl.
CPC .............. *A61K 47/34* (2013.01); *A61J 1/2089* (2013.01); *A61K 9/0024* (2013.01); *A61K 9/1647* (2013.01); *A61K 9/5153* (2013.01); *A61K 38/08* (2013.01); *A61K 38/09* (2013.01); *A61K 47/22* (2013.01); *C08G 63/00* (2013.01); *C08G 63/08* (2013.01); *C08L 67/02* (2013.01); *C08L 67/04* (2013.01); *A61K 47/48915* (2013.01)

(58) Field of Classification Search
CPC ........ C08L 67/04; C08L 67/02; A61K 9/5153; A61K 9/1647; A61K 47/48915
See application file for complete search history.

(56) References Cited

U.S. PATENT DOCUMENTS

| | | | |
|---|---|---|---|
| 3,284,417 A | 11/1966 | Hostettler et al. | |
| 3,839,297 A | 10/1974 | Wasserman et al. | |
| 4,040,420 A | 8/1977 | Speer | |
| 4,137,921 A | 2/1979 | Okuzumi et al. | |
| 4,652,441 A | 3/1987 | Okada et al. | |
| 4,767,628 A | 8/1988 | Hutchinson | |
| 4,835,139 A | 5/1989 | Tice et al. | |
| 4,849,228 A | 7/1989 | Yamamoto et al. | |
| 4,938,763 A | 7/1990 | Dunn et al. | |
| 5,198,220 A | 3/1993 | Damani | |
| 5,278,201 A | 1/1994 | Dunn et al. | |
| 5,278,202 A | 1/1994 | Dunn et al. | |
| 5,324,519 A | 6/1994 | Dunn et al. | |
| 5,575,987 A | 11/1996 | Kamei et al. | |
| 5,631,020 A | 5/1997 | Okada et al. | |
| 5,672,659 A * | 9/1997 | Shalaby ................... | C07K 7/23 424/489 |
| 5,702,716 A | 12/1997 | Dunn et al. | |

(Continued)

FOREIGN PATENT DOCUMENTS

| | | |
|---|---|---|
| EP | 0052510 A2 | 5/1982 |
| EP | 0430474 A | 11/1989 |

(Continued)

OTHER PUBLICATIONS

"", FDA Orange Book—Leuprolide Acetate, (Dec. 2009).
"", FDA Orange Book—Lupron Depot Exclusivity, (Dec. 2009).
"", In: Goodman & Gilman's The Pharmacological Basis of Therapeutics, Tenth Edition. McGraw-Hill, (2001), 3-5, 24-25, 31-34.
"Additional experimental data", 6 pgs.
"U.S. Appl. No. 09/181,355, Advisory Action mailed Mar. 16, 2000", 3 pgs.
"U.S. Appl. No. 09/181,355, Final Office Action mailed Nov. 23, 1999", 10 pgs.
"U.S. Appl. No. 09/181,355, Notice of Allowance mailed May 31, 2000", 7 pgs.
"U.S. Appl. No. 09/181,355, Response filed Feb. 23, 2000 to Final Office Action mailed Nov. 23, 1999", 7 pgs.

(Continued)

*Primary Examiner* — Gregory Listvoyb
(74) *Attorney, Agent, or Firm* — Schwegman Lundberg & Woessner, P.A.

(57) ABSTRACT

A polymer and a method for its preparation are provided. The polymer comprises poly(lactide), poly(lactide/glycolide) or poly(lactic acid/glycolic acid) segments bonded by ester linkages to both ends of an alkanediol core unit. The polymer is for use in a controlled release formulation for a medicament, preferably leuprolide acetate. The controlled release formulation is administered to a patient as a subcutaneous depot of a flowable composition comprising the polymer, a biocompatible solvent, and the medicament. Controlled release formulations comprising the polymer release leuprolide for treatment of prostate cancer patients over periods of 3-6 months.

14 Claims, No Drawings

(56) References Cited

U.S. PATENT DOCUMENTS

| | | | |
|---|---|---|---|
| 5,716,640 | A | 2/1998 | Kamei et al. |
| 5,728,396 | A | 3/1998 | Peery et al. |
| 5,744,153 | A | 4/1998 | Yewey et al. |
| 5,747,637 | A | 5/1998 | Shinoda et al. |
| 5,770,559 | A | 6/1998 | Manning et al. |
| 5,780,044 | A | 7/1998 | Yewey et al. |
| 5,945,115 | A | 8/1999 | Dunn et al. |
| 5,990,194 | A | 11/1999 | Dunn et al. |
| 6,036,976 | A | 3/2000 | Takechi et al. |
| 6,083,916 | A | 7/2000 | Nonomura et al. |
| 6,143,314 | A | 11/2000 | Chandrashekar et al. |
| 6,238,687 | B1 | 5/2001 | Mao et al. |
| 6,395,293 | B2 | 5/2002 | Polson et al. |
| 6,413,536 | B1 | 7/2002 | Gibson et al. |
| 6,555,645 | B1 | 4/2003 | Ikeda et al. |
| 6,565,874 | B1 | 5/2003 | Dunn et al. |
| 6,630,155 | B1 | 10/2003 | Chandrashekar et al. |
| 6,773,714 | B2 | 8/2004 | Dunn et al. |
| 8,470,359 | B2 | 6/2013 | Dunn |
| 8,486,455 | B2 | 7/2013 | Dunn et al. |
| 8,840,916 | B2 | 9/2014 | Dunn et al. |
| 8,877,225 | B2 * | 11/2014 | Norton ................. A61K 9/0024 424/423 |
| 9,254,307 | B2 | 2/2016 | Dunn et al. |
| 9,283,282 | B2 | 3/2016 | Dunn |
| 2004/0229912 | A1 | 11/2004 | Dunn et al. |
| 2007/0117959 | A1 | 5/2007 | Shastri et al. |
| 2008/0138399 | A1 | 6/2008 | Gonda |
| 2008/0194663 | A1 | 8/2008 | Dunn |
| 2010/0226954 | A1 | 9/2010 | Dunn et al. |
| 2010/0234305 | A1 | 9/2010 | Dunn et al. |
| 2013/0210853 | A1 | 8/2013 | Norton et al. |
| 2013/0303722 | A1 | 11/2013 | Dunn |
| 2014/0357574 | A1 | 12/2014 | Dunn |
| 2015/0150937 | A1 | 6/2015 | Dunn et al. |
| 2016/0106805 | A1 | 4/2016 | Dunn et al. |

FOREIGN PATENT DOCUMENTS

| | | | |
|---|---|---|---|
| EP | 0430474 | A1 | 6/1991 |
| EP | 0539751 | A | 10/1991 |
| EP | 0539751 | A1 | 5/1993 |
| JP | 03271213 | | 12/1991 |
| JP | 03271219 | | 12/1991 |
| JP | 05305135 | | 11/1993 |
| JP | 09511741 | | 11/1997 |
| WO | WO-9003768 | A1 | 4/1990 |
| WO | WO-9527481 | A1 | 10/1995 |
| WO | WO-9535097 | A1 | 12/1995 |
| WO | WO-0040259 | A1 | 7/2000 |

OTHER PUBLICATIONS

"U.S. Appl. No. 09/181,355, Response filed Apr. 20, 2000 to Advisory Action mailed Mar. 16, 2000", 6 pgs.
"U.S. Appl. No. 09/643,289, Advisory Action mailed Jul. 30, 2002", 2 pgs.
"U.S. Appl. No. 09/643,289, Final Office Action mailed Mar. 20, 2002", 8 pgs.
"U.S. Appl. No. 09/643,289, Non Final Office Action mailed May 25, 2001", 8 pgs.
"U.S. Appl. No. 09/643,289, Non Final Office Action mailed Nov. 13, 2002", 5 pgs.
"U.S. Appl. No. 09/643,289, Notice of Allowance mailed May 6, 2003", 6 pgs.
"U.S. Appl. No. 09/643,289, PTO Response to 312 Amendment mailed Aug. 6, 2003", 2 pgs.
"U.S. Appl. No. 09/643,289, Response filed Feb. 26, 2003 to Non Final Office Action mailed Nov. 13, 2002", 15 pgs.
"U.S. Appl. No. 09/643,289, Response filed Jun. 20, 2002 to Final Office Action mailed Mar. 20, 2002", 20 pgs.
"U.S. Appl. No. 09/643,289, Response filed Nov. 20, 2001 to Non Final Office Action mailed May 5, 2001", 23 pgs.

"U.S. Appl. No. 09/666,174, Final Office Action mailed Aug. 10, 2001", 10 pgs.
"U.S. Appl. No. 09/666,174, Non Final Office Action mailed Mar. 19, 2001", 9 pgs.
"U.S. Appl. No. 09/666,174, Response filed Jun. 19, 2001 to Non Final Office Action mailed Mar. 19, 2001", 9 pgs.
"U.S. Appl. No. 09/711,758, 312 Amendment filed Mar. 4, 2003", 2 pgs.
"U.S. Appl. No. 09/711,758, Final Office Action mailed Feb. 4, 2002", 10 pgs.
"U.S. Appl. No. 09/711,758, Non Final Office Action mailed Jun. 17, 2002", 8 pgs.
"U.S. Appl. No. 09/711,758, Non Final Office Action mailed Jul. 2, 2001", 10 pgs.
"U.S. Appl. No. 09/711,758, Notice of Allowance mailed Jan. 8, 2003", 6 pgs.
"U.S. Appl. No. 09/711,758, PTO Resonse to 312 Amendment mailed Apr. 13, 2003", 2 pgs.
"U.S. Appl. No. 09/711,758, Response filed May 6, 2002 to Final Office Action mailed Feb. 4, 2002", 17 pgs.
"U.S. Appl. No. 09/711,758, Response filed Oct. 14, 2002 to Non Final Office Action mailed Jun. 17, 2002", 13 pgs.
"U.S. Appl. No. 09/711,758, Response filed Nov. 2, 2001 to Non Final Office Action mailed Jul. 2, 2001", 105 pgs.
"U.S. Appl. No. 10/373,400, Non Final Office Action mailed Oct. 28, 2003", 8 pgs.
"U.S. Appl. No. 10/373,400, Notice of Allowance mailed Mar. 18, 2004", 5 pgs.
"U.S. Appl. No. 10/373,400, Preliminary Amendment filed Apr. 3, 2003", 2 pgs.
"U.S. Appl. No. 10/373,400, Response filed Feb. 20, 2004 to Non Final Office Action mailed Oct. 28, 2003", 17 pgs.
"U.S. Appl. No. 10/872,671, Non Final Office Action mailed May 4, 2006", 10 pgs.
"U.S. Appl. No. 10/872,671, Response filed Oct. 4, 2006 to Non Final Office Action mailed May 4, 2006", 10 pgs.
"U.S. Appl. No. 11/469,392, Advisory Action mailed Feb. 8, 2012", 3 pgs.
"U.S. Appl. No. 11/469,392, Advisory Action mailed Mar. 16, 2011", 3 pgs.
"U.S. Appl. No. 11/469,392, Final Office Action mailed Jul. 5, 2011", 8 pgs.
"U.S. Appl. No. 11/469,392, Final Office Action mailed Dec. 21, 2011", 8 pgs.
"U.S. Appl. No. 11/469,392, Final Office Action mailed Dec. 29, 2010", 11 pgs.
"U.S. Appl. No. 11/469,392, Non Final Office Action mailed Jul. 3, 2012", 12 pgs.
"U.S. Appl. No. 11/469,392, Non-Final Office Action mailed Jul. 20, 2010", 9 pgs.
"U.S. Appl. No. 11/469,392, Notice of Allowance mailed Feb. 27, 2013", 9 pgs.
"U.S. Appl. No. 11/469,392, Preliminary Amendment mailed Mar. 1, 2012", 12 pgs.
"U.S. Appl. No. 11/469,392, Response flied Jan. 13, 2012 to Final Office Action mailed Dec. 21, 2011", 12 pgs.
"U.S. Appl. No. 11/469,392, Response filed Feb. 24, 2011 to Final Office Action mailed Dec. 29, 2010", 14 pgs.
"U.S. Appl. No. 11/469,392, Response filed May 31, 2011 to Advisory Action mailed Mar. 16, 2011", 23 pgs.
"U.S. Appl. No. 11/469,392, Response filed Jun. 30, 2010 to Restriction Requirement mailed Jun. 9, 2010", 10 pgs.
"U.S. Appl. No. 11/469,392, Response filed Sep. 27, 2011 to Non Final Office Action mailed Jul. 5, 2011", 17 pgs.
"U.S. Appl. No. 11/469,392, Response fiied Oct. 7, 2010 to Non Final Office Action mailed Jul. 20, 2010", 14 pgs.
"U.S. Appl. No. 11/469,392, Response filed Dec. 3, 2012 to Non Final Office Action mailed Jul. 3, 2012", 19 pgs.
"U.S. Appl. No. 11/469,392, Restriction Requirement mailed Jun. 9, 2010", 7 pgs.
"U.S. Appl. No. 11/643,505, Final Office Action mailed Dec. 21, 2009", 11 pgs.

(56) References Cited

OTHER PUBLICATIONS

"U.S. Appl. No. 11/643,505, Non Final Office Action mailed Apr. 1, 2009", 12 pgs.
"U.S. Appl. No. 11/643,505, Preliminary Amendment filled Dec. 21, 2006", 5 pgs.
"U.S. Appl. No. 11/643,505, Response filed Sep. 30, 2009 to Non Final Office Action mailed Apr. 1, 2009", 13 pgs.
"U.S. Appl. No. 12/784,304, Non Final Office Action mailed Mar. 6, 2012", 5 pgs.
"U.S. Appl. No. 12/784,304, Notice of Allowance mailed May 28, 2013", 9 pgs.
"U.S. Appl. No. 12/784,304, Notice of Allowance mailed Nov. 5, 2012", 7 pgs.
"U.S. Appl. No. 12/784,304, Response filed Jun. 6, 2012 to Non Final Office Action mailed Mar. 6, 2012", 5 pgs.
"U.S. Appl. No. 12/784,343, Advisory Action mailed Feb. 7, 2014", 2 pgs.
"U.S. Appl. No. 12/784,343, Advisory Action mailed Aug. 20, 2014", 3 pgs.
"U.S. Appl. No. 12/784,343, Advisory Action mailed Dec. 7, 2012", 3 pgs.
"U.S. Appl. No. 12/784,343, Final Office Action mailed Jun. 19, 2014", 7 pgs.
"U.S. Appl. No. 12/784,343, Final Office Action mailed Sep. 27, 2013", 8 pgs.
"U.S. Appl. No. 12/784,343, Final Office Action mailed Dec. 16, 2013", 5 pgs.
"U.S. Appl. No. 12/784,343, Non Final Office Action mailed Mar. 7, 2012", 6 pgs.
"U.S. Appl. No. 12/784,343, Non Final Office Action mailed Apr. 9, 2015", 7 pgs.
"U.S. Appl. No. 12/784,343, Non Final Office Action mailed May 23, 2013", 8 pgs.
"U.S. Appl. No. 12/784,343, Notice of Allowance mailed Oct. 2, 2015", 7 pgs.
"U.S. Appl. No. 12/784,343, Preliminary Amendment and Response filed Nov. 19, 2014 to Advisory Action mailed Aug. 20, 2014", 27 pgs.
"U.S. Appl. No. 12/784,343, Preliminary Amendment filed May 20, 2010", 11 pgs.
"U.S. Appl. No. 12/784,343, Response filed Jan. 20, 2014 to Final Office Action mailed Dec. 16, 2013", 9 pgs.
"U.S. Appl. No. 12/784,343, Response filed Feb. 27, 2013 to Advisory Action mailed Dec. 7, 2012", 14 pgs.
"U.S. Appl. No. 12/784,343, Response filed May 19, 2015 to Non Final Office Action mailed Apr. 9, 2015", 6 pgs.
"U.S. Appl. No. 12/784,343, Response filed Jun. 7, 2012 to Non Final Office Action mailed Mar. 7, 2012", 5 pgs.
"U.S. Appl. No. 12/784,343, Response filed Jul. 14, 2014 to Final Office Action mailed Jun. 19, 2014", 8 pgs.
"U.S. Appl. No. 12/784,343, Response filed Nov. 4, 2013 to Non Final Office Action mailed May 23, 2013", 6 pgs.
"U.S. Appl. No. 12/784,343, Response filed Nov. 27, 2012 to Final Office Action mailed Sep. 27, 2012", 6 pgs.
"U.S. Appl. No. 13/900,338, Final Office Action mailed Apr. 11, 2014", 5 pgs.
"U.S. Appl. No. 13/900,338, Non Final Office Action mailed Sep. 23, 2013", 7 pgs.
"U.S. Appl. No. 13/900,338, Notice of Allowance mailed May 21, 2014", 5 pgs.
"U.S. Appl. No. 13/900,338, Preliminary Amendment filed Aug. 22, 2013", 7 pgs.
"U.S. Appl. No. 13/900,338, Response filed Apr. 15, 2014 to Final Office Action mailed Apr. 11, 2014", 3 pgs.
"U.S. Appl. No. 13/900,338, Response filed Dec. 23, 2013 to Non Final Office Action mailed Sep. 23, 2013", 5 pgs.
"U.S. Appl. No. 14/463,353, Non Final Office Action mailed Mar. 24, 2015", 11 pgs.
"U.S. Appl. No. 14/463,353, Notice of Allowance mailed Nov. 6, 2015", 7 pgs.
"U.S. Appl. No. 14/463,353, Preliminary Amendment filed Aug. 20, 2014", 6 pgs.
"Application Serial No. 2000-577985 Office Action maiied Mar. 16, 2010", (w/ English Translation), 14 pgs.
"Application Serial No. 2000-577985 Response filed Jul. 2, 2010 to Office Action mailed Mar. 16, 2010", (w/ English Translation of Amended Claims), 11 pgs.
"U.S. Appl. No. 24/463,353. Response filed Jun. 24, 2015 to NonFinal Action mailed Mar. 24, 2015", 8 pgs.
"Japanese Application Serial No. 2006-543949, Notice of Allowance mailed Aug. 5, 2010", 3 pgs.
"Lupron Depot(r)", Physicians' Desk Reference(r), 53rd Edition, published by Medical Economics Company, Inc., Montvale, NJ, (1999), 3139-3150.
"Lupron(r), TAP Pharmaceuticals, Inc.", Physicians' Desk Reference(r), 54th Edition, published by Medical Economics Company, Inc., Montvale, NJ, (2000), 3 pgs.
"Physicians' Desk Reference", published by Medical Economics Co., Montvale, New Jersey, (1996), 2555-2559.
Astaneh, Reyhaneh, et al., "Formulation of an Injectable Implant for Peptide Delivery and Mechanistic Study of the Effect of Polymer Molecular Weight on its Release Behavior", DARU, 14(2), (2006), 65-70.
Beck, L R, et al., "Poly(DL-lactide-co-glycolide)/norethisterone microcapsules: an injectable biodegradable contraceptive.", Biol Reprod., 28(1), (Feb. 1983), 186-95.
Chandrashekar, B. L., et al., "Sustained Release of Leuprolide Acetate From an In-Situ Forming Biodegradable Polymeric Implant as the Delivery Vehicle", Proceedings, 26th International Symposium on Controlled Release of Bioactive Materials, 26, (1999), 2 pgs.
Chu, F. M. et al., "A clinical study of 22.5 mg. La-2550: A new subcutaneous depot delivery system for leuprolide acetate for the treatment of prostate cancer", J Urol., 168(3):, (Sep. 2002), 1199-203.
Crawford, E. D, et al., "A 12-month clinical study of LA-2585 (45.0 mg): a new 6-month subcutaneous delivery system for leuprolide acetate for the treatment of prostate cancer.", J Urol., 175(2), (Feb. 2006), 533-6.
Heller, J., "Controlled release of biologically active compounds from bioerodible polymers", Biomaterials, 1(1), (Jan. 1980), 51-57.
Heylin, M., "Chemistry Grads Post Gains in 2005", C & EN—Chemical & Engineering News, 84(30), (2006), 43-52.
Jalil, R., et al., "Biodegradable poly(lactic acid) and poly(lactide-co-glycolide) microcapsules: problems associated with preparative techniques and release properties", J. Microencapsulation, 7(3), (1990), 297-325.
Jarr, E. M., et al., "Sustained Release of Lidocaine from an Injectable Implant System for Treatment of Post-Operative Pain", Proceedings of the International Symp. control Rel. Bioact. Mater, 26, (Jul. 1999), 631-632.
Odian, G., "", In: Principles of Polymerization, New York : Wiley, 3rd Edition, (1991), 20-23.
Okada, H., "One- and Three-Month Release Injectable Microspheres of the LH-RH Superaaonist Leuprorelin Acetate", Advanced Drug Delivery Reviews, 28(1), (1997), 43-70.
Perez-Marreno, R., et al., "A six-month, open-label study assessing a new formulation of leuprolide 7.5 mg for suppression of testosterone in patients with prostate cancer", Clinical Therapeutics, 24(11), (2002), 1902-1914.
Perez-Marreno, R., et al., "A Subcutaneous Delivery System for the Extended Release of Leuprolide Acetate for the Treatment of Prostate Cancer", Expert Opinion in Pharmcother., 5(2), (2004), 447-457.
Ravivarapu, H. B., et al., "Parameters affecting the efficacy of a sustained release polymeric implant of leuprolide", Int J Pharm., 194(2), (Jan. 1, 2000), 181-191.
Ravivarapu, H. B., et al., "Sustained suppression of pituitary-gonadal axis with an injectable, in situ forming implant of leuprolide acetate", J Pharm Sci., 89(6), (Jun. 2000), 732-41.

(56) References Cited

OTHER PUBLICATIONS

Sartor, O., et al., "An Eight-Month Clinical Study of LA-2575 300 mg: A New 4-Month, Subcutaneous Delivery System for Leuprolide Acetate in the Treatment of Prostate Cancer", Urology, 62(2), (2003), 319-323.

Schindler, A., et al., "Biodegradable Polymers for Sustained Drug Delivery", In Contemporary Topics in Polymer Science, vol. 2, (1977), 251-286.

Sharifi, R., et al., "Clinical study of leuprolide depot formulation in the treatment of advanced prostate cancer. The Leuprolide Study Group", The Journal of Urology, 143(1), (Jan. 1, 1990), 68-71.

Tice, T. R., et al., "3-Month and 6-Month Delivery of Peptides (LHRH) From Injectable, Poly(Lactide-Co-Glycolide) Microspheres", Proceedings, International Symposium on Controlled Release of Bioactive Materials, 18, (1991), 467-468.

Tice, T. R., et al., "Biodegradabie controlled-release parental systems", Pharmaceutical Technology, 8(11), (Nov. 1984), 26-35.

Wise, Donald L., et al., "Chapter 12—Lactic/Glycolic Acid Polymers", In: Drug Carriers in Biology and Medicine, Gregoriadis, G., Editor, Academic Press, Inc., New York, NY, (1979), 237-270.

"U.S. Appl. No. 14/619,621, Non Final Office Action mailed Jul. 28, 2016", 14 pgs.

"U.S. Appl. No. 14/619,621, Response filed Jun. 1, 2016 to Restriction Requirement mailed May 5, 2016", 7 pgs.

"U.S. Appl. No. 14/619,621, Restriction Requirement mailed May 5, 2016", 6 pgs.

"U.S. Appl. No. 14/930,387, Non Final Office Action mailed Jun. 16, 2016", 11 pgs.

* cited by examiner

SUSTAINED RELEASE POLYMER

CROSS-REFERENCE TO RELATED APPLICATIONS

This application is a continuation of U.S. application Ser. No. 14/463,353, filed Aug. 19, 2014, which is a continuation of U.S. application Ser. No. 13/900,338, filed May 22, 2013, which is a continuation of U.S. application Ser. No. 11/469,392, filed Aug. 31, 2006, which is a continuation-in-part of U.S. Ser. No. 10/872,671, filed Jun. 21, 2004, publication number US 2004/0229912, which is a continuation of U.S. patent application Ser. No. 10/373,400, filed Feb. 24, 2003 and issued as U.S. Pat. No. 6,773,714, which is a continuation of U.S. application Ser. No. 09/711,758, filed Nov. 13, 2000 and issued as U.S. Pat. No. 6,565,874. All these applications are incorporated by reference herein in their entirety.

FIELD OF THE INVENTION

The field of the invention is a novel polymer composition for use in a sustained release formulation for a medicament, the formulation comprising the composition being emplaced within the tissue of a patient suffering from a malcondition such as prostate cancer.

BACKGROUND OF THE INVENTION

Flowable, polymer-containing compositions useful as biodegradable controlled release formulations for medicinal substances are described, for instance, in U.S. Pat. Nos. 4,938,763; 5,702,716; 5,744,153; 5,990,194; 5,324,519; 6,143,314; 6,630,155; 6,565,874; and 6,773,714. One type of controlled release formulation composition includes a biodegradable, water-insoluble polymer or copolymer and medicament dissolved or dispersed in a bio-compatible organic solvent. These compositions are administered in a flowable, preferably liquid state to the patient, typically via a syringe needle. Once in the body, the polymer of the composition coagulates into a semi-solid mass as at least some of the water-soluble organic solvent diffuses into surrounding tissues. This semi-solid mass of polymer and residual solvent serves to control the release of the medicament as it diffuses out of the polymer mass into surrounding tissues at a fairly constant rate.

This type of controlled release formulation has been found to be particularly useful for treatment of prostate cancer. It is well-known that reduction of serum testosterone levels can inhibit the growth of prostate cancer, and physical castration of prostate cancer patients, while an effective treatment, suffers from unpopularity among the patients. However, certain medicinal compounds have been found to effectively reduce serum testosterone levels without physical castration (orchiectomy) and have thus found use in prolonging the survival of patients afflicted with prostate cancer. One such compound is leuprolide, a synthetic peptide analog that is a "super-agonist" for leutinizing hormone receptors.

Various polymer compositions have been used for leuprolide controlled release formulations, and one group of polymers that have been found to be well-suited for this use are the polyesters of lactic acid and glycolic acid. Copolymers comprising these monomers have been found to possess desirable attributes including low toxicity, non-allergenicity, and biodegradability in living tissue. These copolymers, including poly(lactide/glycolide) and poly(lactic acid-glycolic acid), may be produced by a variety of methods and have a range of properties. For example, see: "One- and Three-Month Release Injectable Microspheres of the LH-RH Superagonist Leuprorelin Acetate," H. Okada (1997), Advanced Drug Delivery Reviews (Elsevier), 28, 43-70; "Biodegradable Polymers for Sustained Drug Delivery," A. Schindler, R. Jeffcoat, G. L. Kimmel, C. G. Pitt, M. E. Wall, and R. Zweidinger (1977), Contemporary Topics in Polymer Science, v. 2, 251-286, (Plenum Publishing Corp.).

There are a number of patents that discuss methods of preparation of such polymers. One synthetic approach to polymers of this type involves the use of an initiator, a distinct compound that at the initial stages of the polymerization reacts with monomeric units. As an initiator is incorporated into the polymer, it is distinct from a catalyst, which accelerates the polymerization reaction but is not incorporated into the product. The publication by Beck et. al. in Biology of Reproduction, 28, 186-195 (1983) describes the use of lauryl alcohol as an initiator to produce lactide/glycolide copolymers with known molecular weights. U.S. Pat. No. 4,137,921 (Okuzumi et al.) discusses the formation of PLG polymers involving the use of a diethyleneglycol initiator of lactide/glycolide polymerization with stannous octanoate as a catalyst. U.S. Pat. No. 3,284,417 (Hostettler et al.) discusses the use of diol initiators for polymerizations of lactones, wherein the lactones having at least 6-8 carbon atoms. U.S. Pat. No. 4,767,628 (Hutchinson) discusses the preparation of lactide-glycolide copolymers using a lactic acid initiator with a stannous octanoate catalyst. Initiators are not always used in the synthesis of polymers of this type. U.S. Pat. No. 3,839,297 (Wasserman et al.) discusses the production of lactide/glycolide copolymers using stannous octanoate catalyst, but with no initiators.

There is an ongoing need for polymers that confer desirable controlled release properties on formulations adapted for the controlled release of medicaments in human patients for treatment of diseases such as prostate cancer.

SUMMARY OF THE INVENTION

The present invention provides a novel biodegradable polymer, specifically a biodegradable thermoplastic polyester, for use in a relatively long-lasting controlled release formulation adapted to provide for the controlled release of a medicament in vivo. The controlled release formulation comprising the biodegradable polymer of the present invention preferably also comprises leuprolide acetate for treatment of human patients afflicted with prostate cancer.

The biodegradable polymer of the present invention is a composition of matter wherein two polylactide polymer segments ("PL polymer segments") or two poly(lactide/glycolide) copolymer segments ("PLG copolymer segments") or two poly(lactic acid/glycolic acid) copolymer segments ("PLGA copolymer segments") or two poly(lactic acid) polymer segments ("PLA polymer segments") are respectively covalently bonded at one end, bearing a carboxyl group, of each segment to the two hydroxyl groups of a non-polymeric alkanediol core. Bonding is by an ester linkage between the carboxy terminus of each of the copolymer segments and one of the two hydroxyl groups of the alkanediol respectively. The structure of the polymer of the present invention can thus be expressed as: HO-(PL polymer segment)-C(O)O-alkane-OC(O)-(PL polymer segment)-OH or HO-(PLG copolymer segment)-C(O)O-alkane-OC(O)-(PLG copolymer segment)-OH or HO-(PLGA copolymer segment)-C(O)O-alkane-OC(O)-(PLGA copolymer segment)-OH or HO-(PLA polymer segment —C(O)O-alkane-OC(O)-(PLA polymer segment)-OH.

The copolymer segments for PLG and PLGA differ owing to the differing starting materials used in their preparation and the manner in which they are incorporated into the growing polymer chain during the polymerization reaction. The PLG segments include substantially only repeating dimer units (-L-L-G-G-L-L-L-L-) wherein L-L represents a ring-opened lactide dimer unit (lactide being the dimeric cyclic ester of lactic acid) and G-G represents a ring-opened glycolide dimer unit (glycolide being the dimeric cyclic ester of glycolic acid), while the PLGA segments include repeating monomer units (-L-G-L-G-L-) wherein G represents a glycolate (glycolic acid) unit and L represents a lactate (lactic acid) unit. The order or distribution of differing units within each PLG or PLGA segment is substantially random, although the relatively higher rate of reaction of G or G-G over L or L-L will place a higher degree of G or G-G close to the alkanediol core for the PLGA or PLG copolymer segments respectively.

The polymerization reaction for a PLG copolymer segment, wherein G-G or L-L units are incorporated into the growing polymer chain, is a ring-opening polymerization of the cyclic dimeric esters with a hydroxyl group of an alkanediol molecule. A hydroxyl group of the alkanediol first reacts with either the G-G or L-L cyclic dimer to form an ester bond between the G-G or L-L open dimer carboxyl group and one of the alkanediol hydroxyl groups. Thus, the open dimer is bonded to the alkanediol at the carboxyl end of the initial unit of what will become the PLG (or PL) copolymer segment, the product having a free hydroxyl group at the other end. This free hydroxyl group then reacts with another G-G or L-L dimer to add another unit to the growing polymer chain. The same process takes place with the second hydroxyl group of the alkanediol core. When the polymerization reaction ceases, the final product is a polymer that has terminal hydroxyl groups but substantially no terminal carboxyl groups, the carboxyl ends of the two copolymer segments being ester-linked to each of the two hydroxyl groups of the alkanediol core. The polymer thus contains substantially no titratable carboxyl groups, and is a neutral not an acidic polymer. A preferred alkanediol initiator is a linear alkane $\alpha,\omega$-diol. A specific example is 1,6-hexanediol.

The polymerization reaction used in the art for preparing PLGA or PLA polymers lacking a core unit is a condensation reaction where the carboxyl group on either a G or L molecule (L only for PLA) reacts with a hydroxyl group on another G or L molecule to form a dimeric open ester with the elimination of water. This linear dimer with a carboxyl group at one end and a hydroxyl group at the other end then reacts with other G or L molecules to form additional ester groups in the growing polymer chain. At the end of this condensation polymerization, the polymer chains all have a carboxyl group at one end of the polymer chain and a hydroxyl group at the other end of the polymer chain. Thus the art polymer made in this manner is an acidic polymer.

However, when an alkanediol core is added at the beginning of the polymerization according to a method of the invention, one of the two alkanediol hydroxyl groups will react with a carboxyl group of either a G or L to form an alkanediol monoester with the carboxyl group of the G or L, the hydroxyl group of the G or L again reacting with a G or L and so on, to form one of the two copolymer segments; the same process takes place with the second alkanediol hydroxyl group yielding the second copolymer segment, the entire process finally providing a polymer with only hydroxyl groups at both ends of the molecular chain. The resultant polymer is neutral and not acidic. A preferred alkanediol initiator or coupling agent is a linear $\alpha,\omega$-diol. A specific example is 1,6-hexanediol.

It has unexpectedly been found that a polymer of the present invention, when incorporated into a controlled release formulation for leuprolide that is emplaced within the tissues of a prostate cancer patient, provides for a surprisingly long-lasting time course of drug release from the formulation. The time period over which sufficient leuprolide is released to maintain chemical castration levels of serum testosterone (0.5 ng/mL) is as long as 120 days or as long as 180 days. This property is highly advantageous from the medical perspective compared to a shorter time period for art polymers, such as 30 days, as it reduces the number of medical procedures a patient must endure in a course of treatment, enhancing patient comfort and convenience and reducing cost.

A polymer of the present invention has a weight average molecular weight of about 6 kD to about 200 kD, preferably about 8 kD to about 100 kD, more preferably from about 15 kD to about 45 kD. The composition of each PLG copolymer segment preferably comprises from about a 45/55 weight ratio to about a 99/1 weight ratio of DL-lactide to glycolide. The composition of each PLGA copolymer segment preferably comprises from about a 45/55 weight ratio to about a 99/1 weight ratio of DL-lactate to glycolate. Alternatively, a polymer of the present invention has the same molecular weight ranges, but comprises PL or PLA polymer segments, wherein lactide (or equivalently, lactate) comprises 100% of the polymer segment.

The present invention further provides methods for the preparation of the polymers. A method according to the present invention comprises contacting an alkanediol with lactide or with a mixture of lactide and glycolide in the presence of a suitable polymerization catalyst such that the alkanediol serves as an initiation site for the polymerization of the lactide and glycolide units thereon. Thus, in a polymer formed by a method of the invention, the alkanediol becomes a core of a polymer with PL or PLG copolymer segments covalently linked to the alkanediol core and substantially only free hydroxyl group terminal ends. Another method according to the present invention comprises contacting an alkanediol with lactate or a mixture of lactate and glycolate in the presence of a suitable condensation polymerization catalyst such that the alkanediol serves as an initiator or coupling agent for the formation of longer chain PLA or PLGA polymers, again with only hydroxyl terminal ends. Thus, in a polymer formed by a method of the invention, the alkanediol becomes a core of a polymer with PLA or PLGA copolymer segments covalently linked to the alkanediol core.

A preferred method of preparation of a polymer of the invention includes contacting the reactants lactide, glycolide and the alkanediol in the presence of a catalyst comprising a tin salt, preferably the tin salt of an organic acid. A specific example of a catalyst is stannous octanoate.

A preferred method of the present invention further comprises contacting the reactants lactide, glycolide and the alkanediol, and the polymerization catalyst, at an elevated temperature. A preferred temperature is about 140° C. The polymerization reaction can be carried out without a solvent, as a neat melt. Further, the polymerization reaction can be carried out in the absence of oxygen, such as under a vacuum or under an inert atmosphere, for example nitrogen.

It has been surprisingly found that a controlled release formulation comprising a polymer according to the present invention is capable of supporting sustained release of a medicament, for example leuprolide, over a relatively long time period. For example, it has been surprisingly found that a controlled release formulation including a polymer according to the present invention when emplaced in a tissue of a patient in need thereof is capable of providing for sustained release of leuprolide for a period of about 90 days, or about 120 days, or about 180 days.

The controlled release formulation according to the present invention comprises a polymer of the invention, a medicament such as leuprolide, and an organic solvent. The organic solvent dissolves the polymer and the medicament. Preferably the organic solvent is water-soluble at least to some degree, such that when a flowable composition comprising the controlled release formulation is emplaced within a tissue of a patient in need thereof, the polymer coagulates from solution as the organic solvent diffuses away into the surrounding aqueous body fluids. This coagulated composition then slowly releases the medicament over a period of time. A type of organic solvent that can be used comprises amides. Specific examples are N-methylpyrrolidone, N,N-dimethylformamide, and N,N-dimethylacetamide.

The polymer of the present invention can be present in any suitable amount in the flowable composition comprising the controlled release formulation. The polyester is preferably present in about 30 wt. % to about 70 wt. % of the flowable composition and more preferably is present in about 35 wt. % to about 60 wt. % of the flowable composition.

DETAILED DESCRIPTION OF THE INVENTION

Reference will now be made in detail to certain features of the invention, examples of which are illustrated in the accompanying structures and formulas. While examples of the invention will be described in conjunction with the enumerated claims, it will be understood that it is not intended to limit the claimed invention to those examples. On the contrary, the invention is intended to cover all alternatives, modifications, and equivalents which may be included within the scope of the present invention as defined by the claims.

References in the specification to "one embodiment", "an embodiment", "a preferred embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

DEFINITIONS

A "polymer" as used herein refers to a macromolecular organic compound that is largely, but not necessarily exclusively, formed of repeating units covalently bonded in a chain, which may be linear or branched. A "repeating unit" is a structural moiety of the macromolecule which is found more than once within the macromolecular structure. Typically, a polymer is composed of a large number of only a few types of repeating units that are joined together by covalent chemical bonds to form a linear backbone, from which substituents may or may not depend in a branching manner. The repeating units can be identical to each other but are not necessarily so. Therefore a structure of the type -A-A-A-A- wherein A is a repeating unit is a polymer, also known as a homopolymer, and a structure of the type -A-B-A-B- or -A-A-A-B-A-A-A-B- wherein A and B are repeating units, is also a polymer, and is sometimes termed a copolymer. A structure of the type -A-A-A-C-A-A-A or A-B-A-C-A-B-A wherein A and B are repeating units but C is not a repeating unit (i.e., C is only found once within the macromolecular structure) is also a polymer under the definition herein. When C is flanked on both sides by repeating units, C is referred to as a "core" or a "core unit." A short polymer, formed of up to about 10 repeating units, is referred to as an "oligomer." There is theoretically no upper limit to the number of repeating units in a polymer, but practically speaking the upper limit for the number of repeating units in a single polymer molecule may be approximately one million. However, in the polymers of the present invention the number of repeating units is typically in the hundreds.

A "copolymer" is a variety of polymer wherein non-identical repeating units are present. A copolymer may be regular or random in the sequence defined by the more than one type of repeating unit. Some types of copolymers are random copolymers, graft copolymers and block copolymers.

A "polymer segment" or a "copolymer segment" as used herein refers to a portion or moiety of a larger molecule wherein that segment is a section of a polymer or a copolymer respectively that is bonded to other portions or moieties to make up the larger molecule. When the polymer segment or a copolymer segment is attached to the larger molecule at only one end of the segment, the end of attachment is the "proximal end" and the other, free end is the "distal end."

A "core" or a "core unit" as used herein refers to a portion or moiety of a polymer that is not itself a copolymer segment, but is incorporated within the polymer chain and has at least one polymer or copolymer segment bonded to it. A core may have two or more polymer or copolymer segments bonded to it. A core may be formed from a molecule that is incorporated into the polymer chain that grows from it during the polymerization reaction.

The term "lactide" as used herein, when referring to the chemical compound itself, for example as the "lactide reagent" or "lactide reactant" means the dimer cyclic ester of lactic acid:

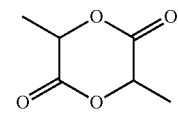

The lactide may be of any configuration at the chiral carbon atoms (bearing the methyl groups) within the meaning of the term herein. It may also be a mixture of molecules with different configurations at the chiral carbon atoms. Thus, lactide may be DD-, DL-, LD-, LL-lactide, or any mixture or combination thereof.

When referring to a polymer such as a poly-lactide or a poly(lactide-glycolide) containing a "lactide" unit, the term "lactide" or "lactide unit" means the ring-opened species consisting of two lactic acid units joined by an ester bond which can be further incorporated into a polymeric chain with other such units or with other types of repeating units.

One end of the lactide unit comprises a carboxyl group that may be bonded to an adjacent atom via an ester linkage, or an amide linkage, or via any other type of bond that a carboxyl group may form. The other end of the lactide unit comprises a hydroxyl group that may be bonded to an adjacent atom via an ester linkage, an ether linkage, or via any other type of bond that a hydroxyl group may form.

A "lactide" in a poly-lactide polymer thus refers to the repeating unit of the polymer that can be viewed structurally as being formed from a pair of lactic acid molecules, with the understanding that the wavy lines indicate points of attachment to neighboring groups:

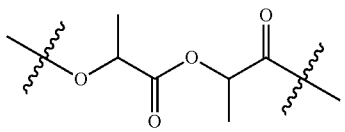

Again, the configuration at the chiral carbon atoms includes any and all possible configurations and mixtures thereof, as described above for the cyclic dimer.

Similarly, the term "glycolide" as used herein, when referring to the chemical compound itself, such as the "glycolide reagent" or the "glycolide reactant" means the dimer cyclic ester of glycolic acid:

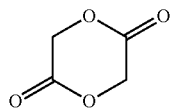

but when referring to a "glycolide" unit in a polymer, the term refers to the repeating unit, a dimer of glycolic acid as shown:

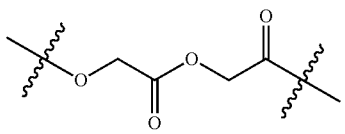

Similarly to the lactide unit, one end of the glycolide unit comprises a carboxyl group that may be bonded to an adjacent atom via an ester linkage, or an amide linkage, or via any other type of bond that a carboxyl group may form, and the other end of the glycolide unit comprises a hydroxyl group that may be bonded to an adjacent atom via an ester linkage, an ether linkage, or via any other type of bond that a hydroxyl group may form.

It should be understood that those in the art comprehend that a "lactide" or a "glycolide" as used herein in either sense is itself a dimer of lactic acid or glycolic acid respectively, either cyclic or linear. In a polymer composed of such dimeric molecular species, the repeating unit as defined herein is therefore formally itself a dimer. Polymers of this type are referred to herein as "polylactide" or "poly(lactide-glycolide)."

It is well-known that there are other polymers known in the art as "poly-lactic acid" or "poly-glycolic acid" that are formed from polymerization of the monomers, either lactate (lactic acid) or glycolate (glycolic acid). There are also copolymers known in the art as "poly(lactic acid-glycolic acid)" or "poly(lactate-glycolate)." In polymers of this type, the repeating unit is a monomer comprising lactic acid, glycolic acid, or both.

When a polymer is formed only of lactic units, or only of glycolic units, the distinction is relatively insignificant except as regards the method by which the polymer is made. However, when a polymer is formed of a mixture of lactic and glycolic units, the distinction is structurally important. For example, a polymer formed of monomeric lactate and glycolate units may comprise sequences of the type -L-G-L-G- where L is a lactate unit and G is a glycolate unit. However, in a polymer formed of lactide and glycolide units, such a sequence would not be found unless rearrangement occurs, because the repeating units join the polymer as pairs of lactic and glycolic units. Thus, sequences such as -L-L-G-G- or -L-L-L-L-G-G-would typify a polymer formed of the lactide and glycolide units, and could by chance also be found in a polymer formed of the monomeric lactate and glycolate units, but in a polymer formed of the dimeric units each type of repeating unit would substantially always comprise a pair of identical monomeric units, so one would not expect to find sequences of the -L-G-L-G- type. Due to this potential ambiguity, it is important to differentiate these two types of polymers.

As used herein, the term "poly(lactide-glycolide)" or the term "PLG" refers solely to a copolymer or a copolymer segment formed of the dimeric repeating units, wherein the dimeric lactide and dimeric glycolide units make up the polymeric chain. A poly(lactide-glycolide) is typically formed through polymerization of the cyclic dimers lactide and glycolide, although theoretically it could be formed through any process wherein dimeric units are incorporated in a given step of the polymerization process. The terms "polylactide" and "PL" refer to a polymer or a polymer segment wherein only lactide repeating units are present. They are formed from polymerization of lactide, and are thus analogous to PLG polymers.

The terms "poly(lactic acid-glycolic acid)," "poly(lactate-glycolate)," or "PLGA" refer solely to a polymer formed of the monomeric repeating units, wherein monomeric lactate and glycolate units make up the polymeric chain. A poly(lactic acid-glycolic acid) is formed by polymerization of monomeric lactic acid and monomeric glycolic acid or derivatives of those acids such as lower alkyl esters. Analogously, the terms "polylactate" and "PLA" refer to polymer or polymer segments wherein only lactate repeating units are present. They are formed by polymerization of lactate.

A "titratable carboxylic acid group" as used herein refers to a carboxylic acid group in free form, that is, not bound as an ester or other derivative, wherein the carboxylic acid group can bear a free proton which may dissociate (ionize) in aqueous solution to form a carboxylate anion and a proton (acid). Therefore, an organic polymer with no titratable carboxylic acid groups is not an acidic polymer, and all carboxylate moieties within the polymer are bonded into esters, amides, or other non-acidic derivatives.

"Alkanediol" as used herein refers to a saturated, branched or straight chain or cyclic alkane diradical of about 4 to about 8 carbon atoms, having two monovalent radical centers derived by the removal of two hydrogen atoms from different carbon atoms of the parent alkane, wherein each monovalent radical center bears a hydroxyl group. Thus, an alkanediol is a dihydroxyalkane. Alkane diradicals include, but are not limited to: 1,4-butylene(-$CH_2CH_2CH_2CH_2$—), 2,3-butylene ($CH_3\dot{C}H\dot{C}HCH_3$), 1,6-hexylene (—$CH_2CH_2CH_2CH_2CH_2CH_2$—), 1,4-cyclohexanedimethyl (—$CH_2$-cyclohexyl-$CH_2$—), and the like. Typical alkanediols of the invention therefore include, but are not limited to, 1,4-butanediol (HOCH$_2$CH$_2$CH$_2$CH$_2$OH), 2,3-butanediol (CH$_3$CH(OH)CH(OH)CH$_3$), 1,6-hexanediol (HOCH$_2$CH$_2$CH$_2$CH$_2$CH$_2$CH$_2$OH), cyclohexane-1,4-dimethanol, and the like. An alkanediol may be optionally substituted with other functional groups on the carbon atoms that form the alkane moiety, including but not limited to groups such as alkoxy, hydroxy, halo, cyano, carboxy, alkylcarboxy, carboxamido, alkyl or dialkyl carboxamido, alkyl or aryl thio, amino, alkyl or dialkyl amino, aryl, or heteroaryl.

An "α,ω-diol" refers to an alkanediol wherein the two hydroxyl groups are disposed respectively on the two terminal carbon atoms of an alkane chain. Typical α,ω-diols are 1,4-butanediol and 1,6-hexanediol. An α,ω-diol comprises two primary hydroxyl groups.

As used herein, the term "inherent viscosity" refers to the standard polymer parameter defined as the natural logarithm of the relative viscosity of a polymer solution divided by the concentration of the polymer in the solution. The relative viscosity is the ratio of the viscosity of the polymer solution to the viscosity of the solvent alone.

A "number average molecular weight" refers to the standard polymer parameter defined as the total weight of a sample divided by the total number of polymer molecules in the sample:

$$\overline{M}_n = \frac{\sum_i N_i M_i}{\sum_i N_i}$$

A "weight average molecular weight" refers to the standard polymer parameter defined as:

$$\overline{M}_w = \frac{\sum_i N_i M_i^2}{\sum_i N_i M_i}$$

where $N_i$ is the number of molecules of molecular weight $M_i$.

The "polydispersity" or "polydispersity index" is the ratio of the weight average molecular weight to the number average molecular weight of a polymer sample, and is a measure of the narrowness or broadness of the distribution of all the individual molecular weights of each polymer molecule in the sample.

DESCRIPTION OF THE INVENTION

The present invention provides a biodegradable polymer for use in a controlled release formulation with a relatively long-lived duration of effectiveness, that is, with a relatively long time period over which a medicament is released from the polymer in therapeutically effective quantities. A flowable composition comprising the novel polymer for use as a controlled release formulation further includes a solvent and a medicament, as is described in U.S. Pat. No. 6,773,714 and documents cited therein, which are incorporated herein by reference. The flowable composition may be used to provide a biodegradable or bioerodible microporous implant formed in situ in animals.

A polymer of the present invention comprises two poly(lactide-glycolide) copolymer segments, or two poly(lactate-glycolate) copolymer segments, or two polylactide polymer segments, or two polylactate polymer segments, respectively covalently bonded to the two hydroxyl groups of an alkanediol core unit. In contrast to many polymers known in the art, the polymers of the invention do not comprise titratable carboxylic acid groups, being hydroxyl-terminated at the distal ends of both PLG or PLGA copolymer segments or PL or PLA polymer segments. This is due to the fact that the carboxyl ends of the copolymer segments are bonded in ester linkages with the hydroxyl groups of the alkanediol core. The absence of titratable carboxylic acid groups in the polymer of the invention means that the chemical functionality present on the terminal ends of the polymer, that is, on the groups at the distal ends of the copolymer segments linked to the alkanediol, are chemically neutral. By chemically neutral it is meant that the groups are not acidic or alkaline, and are not ionizable in aqueous solution at around neutral pH. The chemical neutrality of the polymer is an outstanding advantage of the invention in that no acidic groups are present in the polymer to bring about auto-catalytic degradation through hydrolysis of the ester bonds of the polymer, or to catalyze degradation of a contained medicament, such as the peptide analog leuprolide, or to react with the contained medicament, such as with the amine groups on the peptide analog leuprolide.

A polymer of the present invention can be represented structurally as a compound of Formula (I):

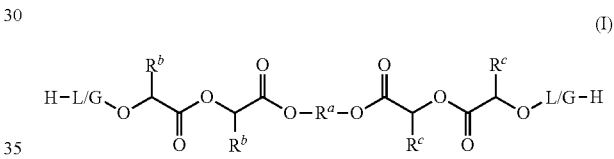

wherein "L/G" signifies a PLG copolymer segment, the H atoms at both distal ends signify the hydrogen atoms borne by the terminal hydroxyl groups, and $R^a$ is an alkylene diradical. The $R^b$ and $R^c$ groups shown on either side of the $R^a$ core moiety may be either hydrogen or methyl, with the proviso that both $R^b$ groups are either hydrogen or methyl concurrently, and both $R^c$ groups are either hydrogen or methyl concurrently, but $R^b$ and $R^c$ need not be the same.

The groups indicated as "L/G" in Formula (I) thus signify lactide/glycolide copolymer segments of the structure:

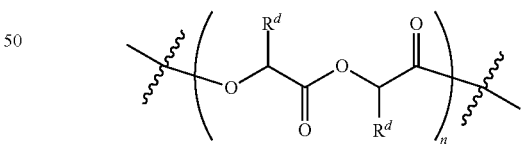

wherein the $R^d$ groups are independently hydrogen or methyl, again with the proviso that as described above, hydrogen substituents or methyl substituents are found in pairs due to their incorporation in pairs as repeating units from the dimeric lactide or glycolide reagents. Other than this requirement of $R^d$ groups being in pairs, methyl groups and hydrogen groups are arranged randomly throughout the copolymer segments L/G, with the understanding that due to the higher rate of reaction of G-G groups, these will tend to be more frequently found adjacent to $R^a$. The wavy lines signify points of attachment to other radicals, for example hydrogen atoms at the distal ends and the core alkanediol hydroxyl groups at the proximal ends. The number of repeating units n range from about 20 up to about 750 for each copolymer segment, providing a polymer of a molecular weight of about 6 kD ranging up to about 200 kD in weight. It is understood that the two L/G copolymer segments need not be identical, and likely are not identical, either in sequence or in the molecular weight of each copolymer segment in a given polymer molecule. Further, the specific composition of each molecule within a sample of the polymer varies in the same manner.

Another polymer of the present invention can be represented structurally as a compound of Formula (II):

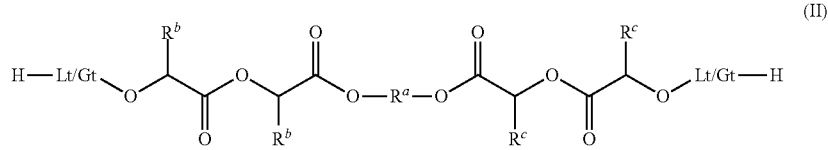

wherein "Lt/Gt" signifies a PLGA copolymer segment, the H atoms at both distal ends signify the hydrogen atoms borne by the terminal hydroxyl groups, and $R^a$ is an alkylene diradical. The $R^b$ and $R^c$ groups shown on either side of the $R^a$ core moiety may be either hydrogen or methyl. There is no restriction that the methyl groups or the hydrogen atoms occur in pairs.

The groups indicated as "Lt/Gt" in Formula (II) thus signify lactate/glycolate copolymer segments of the structure:

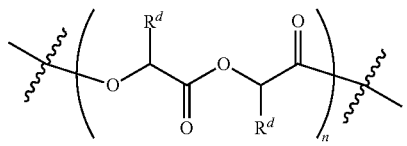

wherein the $R^d$ groups are independently hydrogen or methyl. Methyl groups and hydrogen groups are arranged randomly throughout the copolymer segments L/G, with the understanding that due to the possibly higher rate of reaction of G groups, these may tend to be more frequently found adjacent to $R^a$. The wavy lines signify points of attachment to other radicals, for example hydrogen atoms at the distal ends and the core alkanediol hydroxyl groups at the proximal ends. The number of repeating units n may range from about 20 up to about 185 for each copolymer segment, providing a polymer of a molecular weight of about 6 kD ranging up to about 50 kD in weight. It is understood that the two PLGA copolymer segments need not be identical, and likely are not identical, either in sequence or in the molecular weight of each copolymer segment in a given polymer molecule. Further, the specific composition of each molecule within a sample of the polymer varies in the same manner.

Yet another polymer of the present invention can be represented structurally as a compound of Formula (III):

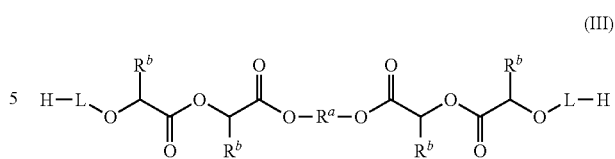

wherein L signifies a polylactide or polylactate polymer segment, the H atoms at both distal ends signify the hydrogen atoms borne by the hydroxyl groups, and $R^a$ is an alkylene diradical. The $R^b$ groups on either side of the $R^a$ core moiety are all methyl.

As is described above, in the polymers of formulas (I), (II), and (III), the distal ends of the copolymer segments comprise hydroxyl groups. The proximal ends of the copolymer segments therefore comprise the carboxyl moieties at the opposite end of the lactide or the glycolide repeating unit, which are linked in ester bonds with hydroxyl groups of the core alkanediols. This structural element is an outstanding feature of the present invention, as it results in the lack of titratable carboxylic acid groups in a polymer of the invention, the product being a neutral polymer.

The core alkanediol can be an α,ω-diol to which the copolymer segments are bonded via the two primary hydroxyl groups. Specific examples of α,ω-diols include 1,4-butanediol, 1,5-pentanediol, 1,6-hexanediol, 1,7-heptanediol and 1,8-octanediol. A particularly preferred alkanediol is 1,6-hexanediol.

The polymer of Formula (I) may be formed by a polymerization reaction wherein the core alkanediol comprising $R^a$ serves as a site for initiation of ring-opening polymerization of the lactide and glycolide reagents. The molar percent, and thus the weight percentage, of the alkanediol that is present in the polymerization reaction has an influence on the molecular weight of the biodegradable polymer that is formed. Use of a higher percentage of the alkanediol in the polymerization reaction provides, on the average, a polymer of lower molecular weight that has relatively shorter PL or PLG copolymer segments linked to the alkanediol core.

A preferred embodiment according to the present invention is a method of preparation of a polymer of Formula (I), comprising contacting an alkanediol, glycolide, lactide, and a catalyst, the catalyst being adapted to catalyze the ring-opening polymerization of the lactide and the glycolide initiated on the alkanediol.

A polymer of the present invention comprising PLG copolymer segments is preferably prepared using a catalyst suitable for ring-opening polymerization of lactide and glycolide. The catalyzed ring opening reaction initially takes place between the lactide or glycolide reagent and a hydroxyl group of the alkanediol core unit such that the lactide or a glycolide unit forms an ester bond. Thus, after the first step of polymerization, only hydroxyl groups on the growing polymer chain continue to be available for further lactide or glycolide addition. As polymerization continues, each step continues to result in formation only of hydroxyl-terminated copolymer segments attached to the alkanediol. In this manner, polymerization takes place until the supply of lactide and glycolide reagents is exhausted, producing the hydroxyl group terminated polymer. It is understood that a polymer of the present invention comprising PL copolymer segments can be made in the same manner, only omitting the glycolide reagent.

The alkanediol can be an $\alpha,\omega$-diol such as 1,6-hexanediol. The alkanediol may be present in the polymerization reaction mixture in amounts ranging from about 0.05% to about 5.0%, preferably from about 0.5% to about 2.0%.

The catalyst may be any catalyst suitable for ring-opening polymerization, but a preferred catalyst is a tin salt of an organic acid. The tin salt may be either in the stannous (divalent) or stannic (tetravalent) form. A particularly preferred catalyst is stannous octanoate. The catalyst may be present in the polymerization reaction mixture in any suitable amount, typically ranging from about 0.01 to 1.0 percent.

The polymerization reaction may be carried out under a variety of conditions of temperature, time and solvent. Alternatively, solvent may be absent and the polymerization be carried out in a neat melt. The polymerization reaction wherein the reactants comprise an alkanediol (such as hexane-1,6-diol), lactide, and glycolide in defined proportions by weight, and a catalyst such as stannous octanoate, is preferably carried out as a neat melt in the absence of oxygen at elevated temperature for a period of at least several hours. Preferably the reaction is carried out at about 140° C. either under vacuum or under an atmosphere of an inert gas such as nitrogen.

The weight percent, and thus mole percent, of lactide or glycolide repeating units in the polymer can be varied by altering the weight percentages of the two reactants present in the polymerization reaction mixture. The properties of the polymer can be changed by variations in the ratio of the lactide to the glycolide monomer components, and by the percent of the alkanediol initiator that is present.

Specifically, the molecular weight range of the polymer can be controlled by the amount of core alkanediol present in the polymerization reaction. The greater the weight percentage, and thus the greater the mole fraction of the alkanediol in the polymerization reaction mixture, the shorter are the chain lengths of the polymers attached to the alkanediol core due to the decreased availability of lactide or glycolide reagent molecules per initiating hydroxyl group.

The ratio of lactide to glycolide in the PLG copolymer segment is within a range of about 45/55 to about 99/1. Preferably, the ratio is within a range of about 70/30 to about 90/10. In a specific example, the ratio is about 75/25. In another specific example the ratio is 85/15.

The weight average molecular weight of the polymer can be about 19 to about 30 kD and the polydispersity index about 1.4 to about 1.8. In a specific example, the weight average molecular weight is about 21 kD and the polydispersity index is about 1.5. The inherent viscosity of the polymer determined in chloroform can be about 0.23 to 0.31 dL/gm. In a specific example the inherent viscosity is 0.25 dL/gm. In another specific example the inherent viscosity is 0.27 dL/gm. In a method of manufacture according to the present invention, these variables may be controlled by a person of skill in the art through controlling the relative starting weights of the lactide and the glycolide in the polymerization reactor, the relative amount of the alkanediol initiator, and the identify and relative quantity of the catalyst used, among other factors.

Another method for preparing a polymer of the invention comprising PLGA copolymer segments comprises contacting an alkanediol, glycolic acid, lactic acid, and a catalyst, the catalyst being adapted to catalyze condensation of the lactate and the glycolate with the alkanediol. Again, the alkanediol can be a linear $\alpha,\omega$-diol. A specific example is hexane-1,6-diol. A typical catalyst for the condensation of lactate and glycolate units is an ion exchange resin, a metal oxide such as zinc oxide or antimony oxide, or the reaction is self-catalyzed by lactic acid and/or glycolic acid.

Yet another method for preparing a polymer of the invention comprising PLA copolymer segments comprises contacting an alkanediol, lactic acid, and a catalyst, the catalyst being adapted to catalyze condensation of the lactic acid with the alkanediol. Again, the alkanediol can be a linear $\alpha,\omega$-diol. A specific example is hexane-1,6-diol. A typical catalyst for the polymerization of lactic acid is an ion exchange resin, a metal oxide such as zinc oxide or antimony oxide, or the reaction is self-catalyzed by lactic acid.

A polymer of the present invention is substantially insoluble in water and body fluid, biocompatible, and biodegradable and/or bioerodible within the body of an animal. A flowable composition comprising a polymer of the invention, a medicament, and an organic solvent, is administered as a liquid or flowable gel to tissue wherein the controlled release implant is formed in situ. The composition is biocompatible and the polymer matrix does not cause substantial tissue irritation or necrosis at the implant site. The implanted composition can be used to deliver leuprolide acetate over a period of time, as is useful for treatment of prostate cancer among other malconditions.

A flowable composition is provided in which a polymer of the invention and a medicament, preferably leuprolide acetate, are dissolved in a biocompatible polar aprotic solvent to form the composition, which can then be administered via a syringe and needle. After administration, the flowable composition coagulates in contact with body fluid to produce a controlled release formulation of the medicament. The properties of the controlled release formulation will typically depend upon the molecular weight and amount of biodegradable thermoplastic polyester present. For example, the molecular weight of the polymer and the amount present in the composition can influence the length of time over which the leuprolide acetate is released into the surrounding tissue. The polymer can be present in about 40 wt. % to about 50 wt. % of the composition; and can have an average molecular weight of about 15,000 to about 30,000, as is disclosed in U.S. Pat. No. 6,773,714. The leuprolide can be present in various quantities, but preferably is present in the range of about 3% to about 15% by weight.

Use of a polymer of the present invention in a controlled release formulation has surprisingly been found to provide for a relatively long duration of release of the medicament from the formulation. For example, using leuprolide acetate as the medicament, it has been unexpectedly found that sustained release of the leuprolide from an implant incorporating a polymer of the present invention persists as long as about 90 days or about 120 days or about 180 days after implantation. Specifically, in preferred embodiments of the present invention, the composition can be used to formulate a three month, a four month, or a six month controlled release delivery system for leuprolide acetate for use in a human patient afflicted with prostate cancer.

When the medicament that is formulated for controlled release is leuprolide acetate, as is used in the treatment of prostate cancer, the efficacy of the release can be monitored by following the serum testosterone level in the patient being treated. The methods used in determining the time period over which release of leuprolide is sustained in such a course of treatment and the results of the experiments in that regard are disclosed in "A Clinical Study of 22.5 mg LA-2550: A New Subcutaneous Depot Delivery System for Leuprolide Acetate for the Treatment of Prostate Cancer," Franklin M. Chu, Maury Jayson, Martin K. Dineen, Ramon Perez, Richard Harkaway, and Robert C. Tyler (2002), *Journal of Urology*, 168(3), 1199-1203, which is incorporated herein by reference. It is disclosed therein that surprisingly, a controlled release formulation of leuprolide acetate comprising a polymer of the present invention, injected subcutaneously to form a depot containing 22.5 mg of leuprolide acetate, is effective in maintaining serum testosterone levels at less than "chemical castration" levels of 50 ng/mL for a period of about 3 months.

The greater duration of leuprolide release in a controlled release formulation of leuprolide acetate comprising a polymer of the present invention relative to controlled release formulations containing other polymers is described in "Sustained Suppression of Pituitary-Gonadal Axis with an Injectable, In Situ Forming Implant of Leuprolide Acetate," Harish B. Ravivarapu, Katie L. Moyer, and Richard L. Dunn (2000), *J. Pharm Sci.*, 89(6), 732-741, which is incorporated herein by reference. In is disclosed therein that surprisingly, controlled release formulations comprising a polymer of the present invention suppress serum testosterone levels to chemical castration levels of less than 50 ng/mL for periods in excess of 3 months, in contrast of controlled release formulations containing other polymers wherein serum testosterone levels were controlled for only about half or less of that time period. Among formulations comprising PLG type polymers (Formulations 2-6). Formulation 2, comprising polymers of the present invention including a hexanediol core, provided for sustained release of leuprolide sufficient to keep blood testosterone levels at chemical castration levels for periods in excess of 100 days, whereas Formulations 4-6 comprising polymers lacking the hexanediol core only suppressed serum testosterone levels for a period of about 40-50 days. The polymers in Formulations 4-6 were those with carboxyl end groups which catalyzed the degradation of the polymer. As a result of the increased degradation rate, these polymers did not remain in the body for a sufficient time to provide the controlled release of leuprolide out to 90 days as needed. Formulation 1 also contained a polymer with carboxyl end groups. This PLA polymer was similar to those used in the Lupron Depot 90 and 120 day controlled release leuprolide products. Although this carboxyl end group polymer was able to last for 90 days, the initial release of leuprolide was not adequate to suppress the testosterone levels below castrate levels as with the 1,6-hexanediol polymer used in Formulation 2. The hydrophobic character of polylactate inhibits the initial hydration and release of the drug, and drug is only released at a sufficient rate after significant polymer degradation has occurred. In contrast, the terminal hydroxyl groups on the 1,6-hexanediol polymer provides the hydrophilicity needed for the polymer implant to quickly hydrate and release the leuprolide during the initial phase of release, and then the polymer slowly degrades without the catalytic action of terminal carboxyl groups. In this way, the release of the drug is maintained for the desired 90 days.

The initial and prolonged period of release of leuprolide when incorporated into the sustained release formulation of the invention, compared to the period of release of leuprolide when incorporated into prior art formulations, was unexpected, but offers the prospect of sustained release formulations that need to be administered to the patient less often. This is evidenced by the surprisingly long duration of controlled release of leuprolide and the resulting suppression of serum testosterone in the patient for a period in excess of 4 months in a controlled release formulation comprising a polymer of the present invention as disclosed in "An Eight-Month Clinical Study of LA-2575 30.0 mg: A New 4-Month, Subcutaneous Delivery System for Leuprolide Acetate in the Treatment of Prostate Cancer," Oliver Sartor, Martin K. Kineen, Ramon Perez-Marreno, Franklin M. Chu, Graham J. Carron, and Robert C. Tyler (2003), *Urology*, 62(2), 319-323, which is incorporated herein by reference. In a study of 90 human patients, a flowable composition (about 0.5 mL) of a controlled release formulation containing 30 mg of leuprolide acetate was injected subcutaneously. Blood samples were collected over a period of 112 days and analyzed for testosterone. It was observed that only 3.6% of the patients failed to maintain chemical castration levels of serum testosterone of less than 50 ng/mL over this time period. Over 90% of the patients had their serum testosterone levels reduced to below 20 ng/mL by this treatment regime.

A controlled release formulation for leuprolide comprising a polymer of the invention wherein a 6-month sustained release is achieved is described in E. David Crawford, et al. (2006), "A 12-month clinical study of LA-2585 (45.0 mg): A new 6-month subcutaneous delivery system for leuprolide acetate for the treatment of prostate cancer," *The Journal of Urology*, 175, 533-536. This publication, incorporated herein by reference, discloses a formulation of leuprolide acetate comprising a polymer of the present invention in a flowable composition, wherein a depot administered approximately every 6 months (168 days) served to keep serum testosterone at chemical castration levels over the period of a year.

All publications, patents, and patent documents are incorporated by reference herein, as though individually incorporated by reference. The invention will now be illustrated with the following non-limiting examples.

EXAMPLES

Example 1

Preparation of Polymer

General Procedure

In a jacketed stainless steel polymerization vessel, appropriate amounts of lactide and glycolide are added and the vessel contents are placed under a nitrogen atmosphere. The temperature of the vessel is increased until the reagents melt. An appropriate amount of an alkanediol is then added, followed by addition of stannous octanoate catalyst. The vessel is then heated at about 135-145° C. under nitrogen atmosphere for about 3-4 hours with constant stirring. Then, to remove unreacted lactide and glycolide monomers, the vessel is evacuated and the monomers are vacuum distilled out of the polymerization mixture. The hot melt is then extruded into cooling pans. After cooling, the solid mass is cryo-ground to a fine powder and dried.

Example 2

Preparation of a Leuprolide Acetate Controlled Release Formulation

A sample of a controlled release formulation for use as a subcutaneous depot was prepared from a polymer prepared as described in Example 1, with a 75/25 lactide to glycolide weight ratio. The polymer and N-methylpyrrolidone were mixed in a 45/55 weight ration until the polymer was completely dissolved in the solvent, then the polymer solution was further mixed with leuprolide acetate to provide a formulation wherein 0.375 gm (about 0.37 mL) of the flowable composition contained 22.5 mg of leuprolide acetate. The mixing was carried out by placing the polymer solution in one syringe, the leuprolide acetate as a lyophilized solid in a second syringe, connecting the two syringes with a luer-lock type connector, and exchanging the contents of the syringes. The solution, a flowable composition, was of sufficient liquidity to be transferred into a patient through a ⅝ inch 20 gauge syringe needle.

Example 3

Treatment of Prostate Cancer Patients with Leuprolide Controlled Release Formulation Comprising Polymer of the Present Invention The solution of Example 2 was injected into the upper right or left abdominal quadrants of 117 patients, 0.37 mL per patient, the patients being afflicted with prostate cancer not previously treated to reduce serum testosterone levels. A depot volume of 0.37 mL was delivered in each case to provide a total of 22.5 mg leuprolide acetate over the period of release. Blood samples were collected and analyzed for testosterone and leutinizing hormone (LH). From a baseline level of about 400-600 ng/dL, testosterone levels dropped to below 20 ng/dL by about day 20 and remained at that level until day 84, when a second depot was injected. Serum testosterone levels were observed to continue to be maintained at or below 20 ng/dL until the end of the study at 168 days. Similarly, LH levels dropped from a pre-treatment baseline of about 10 mIU/mL to below 1 mIU/mL at about 20 days and maintained at that level until the end of the study.

Example 4

Preparation and Treatment of Prostate Cancer Patients with a Leuprolide Acetate Controlled Release Formulation Comprising a Polymer of the Present Invention A controlled release formulation, comprising 30 mg of leuprolide acetate per 0.5 mL of a flowable composition comprising a polymer of the invention and N-methylpyrrolidone, prepared analogously to Example 2, was injected subcutaneously through a ⅝ inch 20 gauge needle into either the upper right or left abdominal quadrant of about 90 patients. Blood samples were collected and analyzed for serum testosterone and LH over a 112 day period, followed by another injection of the same amount and monitoring for an additional 112 day period. Serum testosterone levels dropped below the chemical castration level of 50 ng/mL after about day 20, and maintained at that level throughout the 224 day study period. Only three patients experienced transient "breakthrough" events where serum testosterone levels rose above 50 ng/mL, all of whom had suppression after the second injection at 112 days.

Example 5

Preparation of a 6-Month Leuprolide Acetate Controlled Release Formulation

A polymer of the invention, comprising PLG copolymer segments and a hexanediol core, 85/15 L/G, with an inherent viscosity of 0.27, was dissolved in N-methyl pyrrolidone at a 50 wt % concentration, and radiation-sterilized. Approximately 550 mg of the irradiated polymer solution was transferred to a 1.25 mL female B-Braun syringe. In a 1 mL sterile male syringe, a sterile aqueous solution (0.5 mL) containing 146.8 mg/ml leuprolide acetate was placed and lyophilized to dryness. Immediately prior to injection, the two syringes were coupled and the contents mixed by making approximately 50 reciprocating transfers between the two syringes.

Example 6

Pre-Clinical Study of the 6-Month Formulation

Approximately 500 mg of the formulation of Example 5 containing about 60 mg leuprolide acetate was injected per male beagle with a total of 6 animals in the test group. Serum samples were collected and analyzed for serum testosterone starting prior to injection and continuing regularly through a 211 day time period.

For all 6 beagles, within about 14 days serum testosterone levels had dropped below 0.5 ng/mL, defined as the chemical castration level in humans. Serum testosterone was maintained at this level, with no further injections of the formulation, in excess of 190 days.

Example 7

Clinical Study of the 6-Month Formulation

The 85/15 L/G copolymer described in Example 5 was dissolved in N-methyl-2 pyrrolidone and loaded into 1.2 mL female syringes for sterilization by gamma-irradiation. In a sterile 1 mL male syringe, a sterile-filtered solution of leuprolide acetate was placed and lyophilized to dryness. At the time of use, the two syringes were coupled together and the contents mixed by making approximately 50 reciprocating transfers between the two syringes. The product comprising 45 mg of leuprolide per 0.375 mL of flowable composition was then injected subcutaneously at baseline and at 168 days with a ⅝ inch, 19 gauge hypodermic needle into the upper right or upper left abdominal quadrant of about 111 patients being treated for prostate cancer. Blood samples were collected and analyzed for testosterone and leutinizing hormone (LH). By day 28, 99% of the treatable patients had achieved testosterone suppression. At study completion, 99% of the treatable patients were below medical castrate testosterone levels of 50 ng/dl with 88% at less than 20 ng/dl.

The invention has been described with reference to various specific and preferred embodiments and techniques.

However, it should be understood that many variations and modifications may be made while remaining within the spirit and scope of the invention.

We claim:

1. A polymer for use in manufacture of a controlled release formulation for a drug, comprising a structure of Formula I:

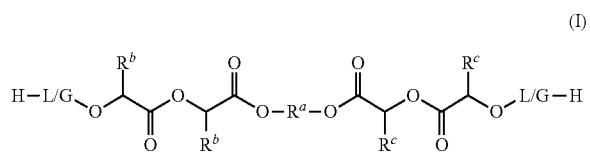

wherein:
- $R^a$ is an alkane diradical comprising about 4 to about 8 carbon atoms;
- $R^b$ is hydrogen or methyl with the proviso that both $R^b$ groups are identical;
- $R^c$ is independently hydrogen or methyl with the proviso that both $R^c$ groups are identical;
- each L/G independently comprises a lactide/glycolide copolymer segment;
- the polymer has substantially no titratable carboxylic acid groups, and
- the polymer has a weight average molecular weight of from about 6 kD to about 200 kD.

2. The polymer of claim 1 wherein L/G comprises a lactide/glycolide copolymer segment with a lactide/glycolide ratio of about 45/55 to about 99/1.

3. The polymer of claim 1 wherein L/G comprises a lactide/glycolide copolymer segment with a lactide/glycolide ratio of about 70/30 to about 90/10.

4. The polymer of claim 1 wherein L/G comprises a lactide/glycolide copolymer segment with a lactide/glycolide ratio of about 85/15.

5. The polymer of claim 1 wherein the weight average molecular weight is about 9 kD to about 100 kD.

6. The polymer of claim 1 wherein the weight average molecular weight is about 25 kD to about 45 kD.

7. The polymer of claim 1 in combination with a drug wherein the combination is a controlled release formulation.

8. The polymer combination of claim 7 wherein the drug is leuprolide.

9. A method of treatment of prostate cancer in a human male patient comprising treating the patient with an effective dose of the polymer combination of claim 8.

10. A method of treatment of claim 9 wherein the treatment s accomplished once every 3 months, 4 months or 6 months.

11. The polymer combination of claim 8 further including an organic solvent which is N-methyl pyrrolidone, N,N-dimethyl formamide or N,N-dimethyl acetamide.

12. The polymer combination of claim 11 wherein the organic solvent is N-methyl pyrrolidone.

13. A method of treatment of prostate cancer in a human male patient comprising administration to the patient an effective dose of a polymer combination of claim 12.

14. A method of treatment of claim 13 wherein the administration is accomplished once every 3 months, 4 months or 6 months.

* * * * *